US012703740B2

(12) United States Patent
Park et al.

(10) Patent No.: US 12,703,740 B2
(45) Date of Patent: Aug. 11, 2026

(54) GKN1 (GASTROKINE 1) SPECIFIC ANTIBODY, AND USE THEREOF

(71) Applicant: THE CATHOLIC UNIVERSITY OF KOREA INDUSTRY-ACADEMIC COOPERATION FOUNDATION, Seoul (KR)

(72) Inventors: Won Sang Park, Seoul (KR); Jung Hwan Yoon, Seoul (KR)

(73) Assignee: THE CATHOLIC UNIVERSITY OF KOREA INDUSTRY-ACADEMIC COOPERATION FOUNDATION, Seoul (KR)

(*) Notice: Subject to any disclaimer, the term of this patent is extended or adjusted under 35 U.S.C. 154(b) by 600 days.

(21) Appl. No.: 18/265,074

(22) PCT Filed: Nov. 29, 2021

(86) PCT No.: PCT/KR2021/017746
§ 371 (c)(1),
(2) Date: Jun. 2, 2023

(87) PCT Pub. No.: WO2022/124665
PCT Pub. Date: Jun. 16, 2022

(65) Prior Publication Data

US 2024/0025976 A1 Jan. 25, 2024

(30) Foreign Application Priority Data

Dec. 11, 2020 (KR) ........................ 10-2020-0173105

(51) Int. Cl.

| | |
|---|---|
| ***A61K 39/395*** | (2006.01) |
| ***C07K 16/18*** | (2006.01) |
| ***C12N 15/63*** | (2006.01) |
| ***G01N 33/5753*** | (2026.01) |

(52) U.S. Cl.
CPC .......... *C07K 16/18* (2013.01); *A61K 39/3955* (2013.01); *C12N 15/63* (2013.01); *G01N 33/5753* (2026.01); *C07K 2317/14* (2013.01); *C07K 2317/565* (2013.01); *C07K 2317/567* (2013.01)

(58) Field of Classification Search
CPC ............................ A61K 39/3955; C07K 16/18
See application file for complete search history.

(56) References Cited

FOREIGN PATENT DOCUMENTS

| | | | | | |
|---|---|---|---|---|---|
| KR | 10-2014-0019646 | A | | 2/2014 | |
| KR | 10-2019-0020364 | | * | 3/2019 | |
| KR | 10-2019-0020364 | A | | 3/2019 | |
| WO | WO-02092758 | A2 | * | 11/2002 | .............. A61P 43/00 |

OTHER PUBLICATIONS

NCBI, Genbank accession No. 4P48_A, Dec. 1, 2020, 3 pages.
Jung Hwan Yoon, et al., "The Role of Gastrokine 1 in Gastric Cancer", Journal Gastric Cancer, 2014, pp. 147-155, vol. 14, No. 3.
Jiang-Wei Xiao, et al., "Relationship Between Expression of Gastrokine 1 and Clinicopathological Characteristics in Gastric Cancer Patients", Asian Pacific Journal of Cancer Prevention, 2012, pp. 5897-5901, vol. 13.
International Search Report for PCT/KR2021/017746 dated Mar. 16, 2022 (PCT/ISA/210).

* cited by examiner

*Primary Examiner* — Xiaozhen Xie
(74) *Attorney, Agent, or Firm* — Sughrue Mion, PLLC

(57) ABSTRACT

The present invention relates to a novel antibody specifically binding to a specific epitope of GKN1 (gastrokine 1) protein, and a gastric cancer diagnostic use thereof. An antibody specific to GKN1 according to the present invention specifically binds to a new epitope, and can be used to confirm the level of GKN1 protein in serum and thereby detect (diagnose) gastric cancer with 100% sensitivity and specificity. Thus, the antibody can be useful for screening and diagnosing gastric cancer.

14 Claims, 11 Drawing Sheets

Specification includes a Sequence Listing.

FIG.1A
Workflow chart
rGKN1 (purity check)
1st Panning
2nd Panning
3rd Panning
ELISA screening
(95 positive binder)
Binder selection
Amplified binder (scFV) fragment
and cloning mini-body (scFV-FC)
Monoclonal anti-GKN1 antibody
production and purification

SEQUENCE LISTING

```
<160> NUMBER OF SEQ ID NOS: 35

<210> SEQ ID NO 1
<211> LENGTH: 26
<212> TYPE: PRT
<213> ORGANISM: Artificial Sequence
<220> FEATURE:
<223> OTHER INFORMATION: GKN1-epitope

<400> SEQUENCE: 1

Glu Lys Lys Leu Gln Gly Lys Gly Pro Gly Gly Pro Pro Pro Lys Gly
1               5                   10                  15

Leu Met Tyr Ser Val Asn Pro Asn Lys Val
            20                  25


<210> SEQ ID NO 2
<211> LENGTH: 5
<212> TYPE: PRT
<213> ORGANISM: Artificial Sequence
<220> FEATURE:
<223> OTHER INFORMATION: VL-CDRL1

<400> SEQUENCE: 2

Asp Ser Trp Tyr Gly
1               5


<210> SEQ ID NO 3
<211> LENGTH: 4
<212> TYPE: PRT
<213> ORGANISM: Artificial Sequence
<220> FEATURE:
<223> OTHER INFORMATION: VL-CDRL2

<400> SEQUENCE: 3

Ala Asn Thr Asn
1


<210> SEQ ID NO 4
<211> LENGTH: 9
<212> TYPE: PRT
<213> ORGANISM: Artificial Sequence
<220> FEATURE:
<223> OTHER INFORMATION: VL-CDRL3

<400> SEQUENCE: 4

Gly Gly Trp Asp Arg Ser Asn Asp Ala
1               5


<210> SEQ ID NO 5
<211> LENGTH: 5
```

```
<212> TYPE: PRT
<213> ORGANISM: Artificial Sequence
<220> FEATURE:
<223> OTHER INFORMATION: VH-CDRH1

<400> SEQUENCE: 5

Ser Tyr Asp Met Ala
1               5


<210> SEQ ID NO 6
<211> LENGTH: 17
<212> TYPE: PRT
<213> ORGANISM: Artificial Sequence
<220> FEATURE:
<223> OTHER INFORMATION: VH-CDRH2

<400> SEQUENCE: 6

Gly Ile Glu Asn Asp Gly Ser Ser Thr Arg Tyr Gly Ser Ala Val Lys
1               5                   10                  15

Gly


<210> SEQ ID NO 7
<211> LENGTH: 17
<212> TYPE: PRT
<213> ORGANISM: Artificial Sequence
<220> FEATURE:
<223> OTHER INFORMATION: VH-CDRH3

<400> SEQUENCE: 7

Lys Thr Ala Asp Ser Cys Ile Gly Gly Cys Ala Ala Gly Trp Ile Asp
1               5                   10                  15

Ala


<210> SEQ ID NO 8
<211> LENGTH: 22
<212> TYPE: PRT
<213> ORGANISM: Artificial Sequence
<220> FEATURE:
<223> OTHER INFORMATION: VL-FR1

<400> SEQUENCE: 8

Leu Thr Gln Pro Ser Ser Val Ser Ala Asn Pro Gly Glu Thr Val Lys
1               5                   10                  15

Ile Thr Cys Thr Gly Asp
            20


<210> SEQ ID NO 9
<211> LENGTH: 16
<212> TYPE: PRT
<213> ORGANISM: Artificial Sequence
<220> FEATURE:
<223> OTHER INFORMATION: VL-FR2

<400> SEQUENCE: 9

Trp Tyr Gln Gln Lys Ala Pro Gly Ser Ala Pro Val Thr Leu Ile Tyr
1               5                   10                  15


<210> SEQ ID NO 10
<211> LENGTH: 35
<212> TYPE: PRT
<213> ORGANISM: Artificial Sequence
<220> FEATURE:
<223> OTHER INFORMATION: VL-FR3

<400> SEQUENCE: 10
```

```
Arg Pro Ser Asn Ile Pro Ser Arg Phe Ser Gly Ser Leu Ser Gly Ser
1               5                   10                  15

Thr Asn Thr Leu Thr Ile Thr Gly Val Gln Val Glu Asp Glu Ala Val
            20                  25                  30

Tyr Phe Cys
        35


<210> SEQ ID NO 11
<211> LENGTH: 14
<212> TYPE: PRT
<213> ORGANISM: Artificial Sequence
<220> FEATURE:
<223> OTHER INFORMATION: VL-FR4

<400> SEQUENCE: 11

Ala Ile Phe Gly Ala Gly Thr Thr Leu Thr Val Leu Gly Gln
1               5                   10


<210> SEQ ID NO 12
<211> LENGTH: 34
<212> TYPE: PRT
<213> ORGANISM: Artificial Sequence
<220> FEATURE:
<223> OTHER INFORMATION: VH-FR1

<400> SEQUENCE: 12

Gly Gly Gly Ser Ala Val Thr Leu Asp Glu Ser Gly Gly Gly Leu Gln
1               5                   10                  15

Thr Pro Gly Gly Gly Leu Ser Leu Val Cys Lys Ala Ser Gly Phe Thr
            20                  25                  30

Phe Ser


<210> SEQ ID NO 13
<211> LENGTH: 14
<212> TYPE: PRT
<213> ORGANISM: Artificial Sequence
<220> FEATURE:
<223> OTHER INFORMATION: VH-FR2

<400> SEQUENCE: 13

Trp Val Arg Gln Ala Pro Gly Gly Gly Leu Glu Trp Val Ala
1               5                   10


<210> SEQ ID NO 14
<211> LENGTH: 31
<212> TYPE: PRT
<213> ORGANISM: Artificial Sequence
<220> FEATURE:
<223> OTHER INFORMATION: VH-FR3

<400> SEQUENCE: 14

Arg Ala Thr Ile Ser Arg Asp Asn Gly Gln Ser Thr Val Arg Leu Gln
1               5                   10                  15

Leu Asn Asn Leu Arg Ala Glu Asp Thr Ala Thr Tyr Tyr Cys Ala
            20                  25                  30


<210> SEQ ID NO 15
<211> LENGTH: 13
<212> TYPE: PRT
<213> ORGANISM: Artificial Sequence
<220> FEATURE:
<223> OTHER INFORMATION: VH-FR4

<400> SEQUENCE: 15
```

```
Trp Gly His Gly Thr Glu Val Ile Val Ser Ser Thr Ser
1               5                   10


<210> SEQ ID NO 16
<211> LENGTH: 105
<212> TYPE: PRT
<213> ORGANISM: Artificial Sequence
<220> FEATURE:
<223> OTHER INFORMATION: VL

<400> SEQUENCE: 16

Leu Thr Gln Pro Ser Ser Val Ser Ala Asn Pro Gly Glu Thr Val Lys
1               5                   10                  15

Ile Thr Cys Thr Gly Asp Asp Ser Trp Tyr Gly Trp Tyr Gln Gln Lys
            20                  25                  30

Ala Pro Gly Ser Ala Pro Val Thr Leu Ile Tyr Ala Asn Thr Asn Arg
        35                  40                  45

Pro Ser Asn Ile Pro Ser Arg Phe Ser Gly Ser Leu Ser Gly Ser Thr
    50                  55                  60

Asn Thr Leu Thr Ile Thr Gly Val Gln Val Glu Asp Glu Ala Val Tyr
65                  70                  75                  80

Phe Cys Gly Gly Trp Asp Arg Ser Asn Asp Ala Ala Ile Phe Gly Ala
                85                  90                  95

Gly Thr Thr Leu Thr Val Leu Gly Gln
            100                 105


<210> SEQ ID NO 17
<211> LENGTH: 131
<212> TYPE: PRT
<213> ORGANISM: Artificial Sequence
<220> FEATURE:
<223> OTHER INFORMATION: VH

<400> SEQUENCE: 17

Gly Gly Gly Ser Ala Val Thr Leu Asp Glu Ser Gly Gly Gly Leu Gln
1               5                   10                  15

Thr Pro Gly Gly Gly Leu Ser Leu Val Cys Lys Ala Ser Gly Phe Thr
            20                  25                  30

Phe Ser Ser Tyr Asp Met Ala Trp Val Arg Gln Ala Pro Gly Gly Gly
        35                  40                  45

Leu Glu Trp Val Ala Gly Ile Glu Asn Asp Gly Ser Ser Thr Arg Tyr
    50                  55                  60

Gly Ser Ala Val Lys Gly Arg Ala Thr Ile Ser Arg Asp Asn Gly Gln
65                  70                  75                  80

Ser Thr Val Arg Leu Gln Leu Asn Asn Leu Arg Ala Glu Asp Thr Ala
                85                  90                  95

Thr Tyr Tyr Cys Ala Lys Thr Ala Asp Ser Cys Ile Gly Gly Cys Ala
            100                 105                 110

Ala Gly Trp Ile Asp Ala Trp Gly His Gly Thr Glu Val Ile Val Ser
        115                 120                 125

Ser Thr Ser
    130


<210> SEQ ID NO 18
<211> LENGTH: 271
<212> TYPE: PRT
<213> ORGANISM: Artificial Sequence
<220> FEATURE:
<223> OTHER INFORMATION: scFv
```

<400> SEQUENCE: 18

```
Leu Thr Gln Pro Ser Ser Val Ser Ala Asn Pro Gly Glu Thr Val Lys
1               5                   10                  15

Ile Thr Cys Thr Gly Asp Asp Ser Trp Tyr Gly Trp Tyr Gln Gln Lys
            20                  25                  30

Ala Pro Gly Ser Ala Pro Val Thr Leu Ile Tyr Ala Asn Thr Asn Arg
        35                  40                  45

Pro Ser Asn Ile Pro Ser Arg Phe Ser Gly Ser Leu Ser Gly Ser Thr
    50                  55                  60

Asn Thr Leu Thr Ile Thr Gly Val Gln Val Glu Asp Glu Ala Val Tyr
65                  70                  75                  80

Phe Cys Gly Gly Trp Asp Arg Ser Asn Asp Ala Ala Ile Phe Gly Ala
                85                  90                  95

Gly Thr Thr Leu Thr Val Leu Gly Gln Ser Ser Arg Ser Ser Cys Gly
            100                 105                 110

Gly Gly Ser Ser Gly Gly Gly Gly Ser Ala Val Thr Leu Asp Glu Ser
        115                 120                 125

Gly Gly Gly Leu Gln Thr Pro Gly Gly Gly Leu Ser Leu Val Cys Lys
    130                 135                 140

Ala Ser Gly Phe Thr Phe Ser Ser Tyr Asp Met Ala Trp Val Arg Gln
145                 150                 155                 160

Ala Pro Gly Gly Gly Leu Glu Trp Val Ala Gly Ile Glu Asn Asp Gly
                165                 170                 175

Ser Ser Thr Arg Tyr Gly Ser Ala Val Lys Gly Arg Ala Thr Ile Ser
            180                 185                 190

Arg Asp Asn Gly Gln Ser Thr Val Arg Leu Gln Leu Asn Asn Leu Arg
        195                 200                 205

Ala Glu Asp Thr Ala Thr Tyr Tyr Cys Ala Lys Thr Ala Asp Ser Cys
    210                 215                 220

Ile Gly Gly Cys Ala Ala Gly Trp Ile Asp Ala Trp Gly His Gly Thr
225                 230                 235                 240

Glu Val Ile Val Ser Ser Thr Ser Gly Gln Ala Gly Gln His His His
                245                 250                 255

His His His Gly Ala Tyr Pro Tyr Asp Val Pro Asp Tyr Ala Ser
            260                 265                 270
```

<210> SEQ ID NO 19
<211> LENGTH: 15
<212> TYPE: DNA
<213> ORGANISM: Artificial Sequence
<220> FEATURE:
<223> OTHER INFORMATION: VL-CDRL1

<400> SEQUENCE: 19
gacagctggt atggc 15

<210> SEQ ID NO 20
<211> LENGTH: 12
<212> TYPE: DNA
<213> ORGANISM: Artificial Sequence
<220> FEATURE:
<223> OTHER INFORMATION: VL-CDRL2

<400> SEQUENCE: 20
gctaacacca ac 12

<210> SEQ ID NO 21

<211> LENGTH: 27
<212> TYPE: DNA
<213> ORGANISM: Artificial Sequence
<220> FEATURE:
<223> OTHER INFORMATION: VL-CDRL3

<400> SEQUENCE: 21
ggtggctggg acaggagcaa tgatgct 27

<210> SEQ ID NO 22
<211> LENGTH: 15
<212> TYPE: DNA
<213> ORGANISM: Artificial Sequence
<220> FEATURE:
<223> OTHER INFORMATION: VH-CDRH1

<400> SEQUENCE: 22
agttatgaca tggcc 15

<210> SEQ ID NO 23
<211> LENGTH: 54
<212> TYPE: DNA
<213> ORGANISM: Artificial Sequence
<220> FEATURE:
<223> OTHER INFORMATION: VH-CDRH2

<400> SEQUENCE: 23
ggtattgaga atgatggtag tagcacaaga tacgggtcgg cggtgaaggg ccgt 54

<210> SEQ ID NO 24
<211> LENGTH: 54
<212> TYPE: DNA
<213> ORGANISM: Artificial Sequence
<220> FEATURE:
<223> OTHER INFORMATION: VH-CDRH3

<400> SEQUENCE: 24
actgctgata gttgtattgg gggttgtgct gctggttgga tcgacgcatg gggc 54

<210> SEQ ID NO 25
<211> LENGTH: 66
<212> TYPE: DNA
<213> ORGANISM: Artificial Sequence
<220> FEATURE:
<223> OTHER INFORMATION: VL-FR1

<400> SEQUENCE: 25
ctgactcagc cgtcctcggt gtcagcgaac ccaggagaaa ccgtcaagat cacctgcacg 60
ggggat 66

<210> SEQ ID NO 26
<211> LENGTH: 48
<212> TYPE: DNA
<213> ORGANISM: Artificial Sequence
<220> FEATURE:
<223> OTHER INFORMATION: VL-FR2

<400> SEQUENCE: 26
tggtaccagc agaaggcacc tggcagtgcc cctgtcactc tgatctat 48

<210> SEQ ID NO 27
<211> LENGTH: 105
<212> TYPE: DNA
<213> ORGANISM: Artificial Sequence
<220> FEATURE:
<223> OTHER INFORMATION: VL-FR3

<400> SEQUENCE: 27
agaccctcga acatcccttc acgattctcc ggttccctat ccggctccac aaacacatta 60
accatcactg ggtccaagt cgaggacgag gctgtctatt tctgt 105

<210> SEQ ID NO 28
<211> LENGTH: 42
<212> TYPE: DNA
<213> ORGANISM: Artificial Sequence
<220> FEATURE:
<223> OTHER INFORMATION: VL-FR4

<400> SEQUENCE: 28
gctatatttg gggccgggac aaccctgacc gtcctaggtc ag 42

<210> SEQ ID NO 29
<211> LENGTH: 102
<212> TYPE: DNA
<213> ORGANISM: Artificial Sequence
<220> FEATURE:
<223> OTHER INFORMATION: VH-FR1

<400> SEQUENCE: 29
ggtggcggtt ccgccgtgac gttggacgag tccgggggcg gcctccagac gcccggagga 60
gggctcagcc tcgtctgcaa ggcctccggg ttcaccttca gc 102

<210> SEQ ID NO 30
<211> LENGTH: 42
<212> TYPE: DNA
<213> ORGANISM: Artificial Sequence
<220> FEATURE:
<223> OTHER INFORMATION: VH-FR2

<400> SEQUENCE: 30
tgggtgcgac aggcacccgg aggagggctg gagtgggtcg cg 42

<210> SEQ ID NO 31
<211> LENGTH: 93
<212> TYPE: DNA
<213> ORGANISM: Artificial Sequence
<220> FEATURE:
<223> OTHER INFORMATION: VH-FR3

<400> SEQUENCE: 31
gccaccatct cgagggacaa cgggcagagc acagtgaggc tgcagctgaa caaccttagg 60
gctgaggaca ccgccaccta ctactgcgcc aaa 93

<210> SEQ ID NO 32
<211> LENGTH: 39
<212> TYPE: DNA
<213> ORGANISM: Artificial Sequence
<220> FEATURE:
<223> OTHER INFORMATION: VH-FR4

<400> SEQUENCE: 32
cacgggaccg aagtcatcgt ctcctccact agtggccag 39

<210> SEQ ID NO 33
<211> LENGTH: 315
<212> TYPE: DNA
<213> ORGANISM: Artificial Sequence
<220> FEATURE:
<223> OTHER INFORMATION: VL

<400> SEQUENCE: 33

```
ctgactcagc cgtcctcggt gtcagcgaac ccaggagaaa ccgtcaagat cacctgcacg     60
ggggatgaca gctggtatgg ctggtaccag cagaaggcac ctggcagtgc ccctgtcact    120
ctgatctatg ctaacaccaa cagaccctcg aacatccctt cacgattctc cggttcccta    180
tccggctcca caaacacatt aaccatcact ggggtccaag tcgaggacga ggctgtctat    240
ttctgtggtg gctgggacag gagcaatgat gctgctatat ttggggccgg gacaaccctg    300
accgtcctag gtcag                                                     315
```

<210> SEQ ID NO 34
<211> LENGTH: 399
<212> TYPE: DNA
<213> ORGANISM: Artificial Sequence
<220> FEATURE:
<223> OTHER INFORMATION: VH

<400> SEQUENCE: 34

```
ggtggcggtt ccgccgtgac gttggacgag tccgggggcg gcctccagac gcccggagga     60
gggctcagcc tcgtctgcaa ggcctccggg ttcaccttca gcagttatga catggcctgg    120
gtgcgacagg cacccggagg agggctggag tgggtcgcgg gtattgagaa tgatggtagt    180
agcacaagat acgggtcggc ggtgaagggc cgtgccacca tctcgaggga caacgggcag    240
agcacagtga ggctgcagct gaacaacctt agggctgagg acaccgccac ctactactgc    300
gccaaaactg ctgatagttg tattgggggt tgtgctgctg gttggatcga cgcatggggc    360
cacgggaccg aagtcatcgt ctcctccact agtggccag                           399
```

<210> SEQ ID NO 35
<211> LENGTH: 813
<212> TYPE: DNA
<213> ORGANISM: Artificial Sequence
<220> FEATURE:
<223> OTHER INFORMATION: scFv

<400> SEQUENCE: 35

```
ctgactcagc cgtcctcggt gtcagcgaac ccaggagaaa ccgtcaagat cacctgcacg     60
ggggatgaca gctggtatgg ctggtaccag cagaaggcac ctggcagtgc ccctgtcact    120
ctgatctatg ctaacaccaa cagaccctcg aacatccctt cacgattctc cggttcccta    180
tccggctcca caaacacatt aaccatcact ggggtccaag tcgaggacga ggctgtctat    240
ttctgtggtg gctgggacag gagcaatgat gctgctatat ttggggccgg gacaaccctg    300
accgtcctag gtcagtcctc tagatcttcc tgcggtggtg gcagctccgg tggtggcggt    360
tccgccgtga cgttggacga gtccgggggc ggcctccaga cgcccggagg agggctcagc    420
ctcgtctgca aggcctccgg gttcaccttc agcagttatg acatggcctg ggtgcgacag    480
gcacccggag gagggctgga gtgggtcgcg ggtattgaga atgatggtag tagcacaaga    540
tacgggtcgg cggtgaaggg ccgtgccacc atctcgaggg acaacgggca gagcacagtg    600
aggctgcagc tgaacaacct tagggctgag gacaccgcca cctactactg cgccaaaact    660
gctgatagtt gtattggggg ttgtgctgct ggttggatcg acgcatgggg ccacgggacc    720
gaagtcatcg tctcctccac tagtggccag gccggccagc accatcacca tcaccatggc    780
gcatacccgt acgacgttcc ggactacgct tct                                 813
```

GKN1 (GASTROKINE 1) SPECIFIC ANTIBODY, AND USE THEREOF

CROSS REFERENCE TO RELATED APPLICATIONS

This application is a National Stage of International Application No. PCT/KR2021/017746 filed Nov. 29, 2021, claiming priority based on Korean Patent Application No. 10-2020-0173105 filed Dec. 11, 2020, the entire disclosures of which are incorporated herein by reference.

SEQUENCE LISTING

The content of the electronically submitted sequence listing, file name: Q286884_Sequence_Listing_As_Filed.txt; size: 13,903 bytes; and date of creation: Jun. 1, 2023, filed herewith, is incorporated herein by reference in its entirety.

TECHNICAL FIELD

The present invention relates to a novel antibody specifically binding to a specific epitope of GKN1 protein and a gastric cancer diagnostic use thereof.

BACKGROUND ART

Cancer is a condition in which the proliferation and death of cells are not normally regulated by various changes in gene expression, and the abnormal growth of cells is caused, and infiltrates and destroys adjacent tissues, metastasizes to other regions, and eventually leads to death. The cause of cancer, that is, a mechanism through which normal cells are transformed into cancer cells, has not been precisely identified, but as far as it is concerned, it has been known that external factors such as environmental factors, chemicals, radiation, and viruses, and internal factors such as genetic factors and immunological factors are complicatedly involved to cause the cancer. The cancer is largely classified into blood cancer showing abnormality in the number of blood cells and solid cancer in the form of a mass of cells having certain hardness and shape in the body. The cancer may occur in almost all parts of the body, such as blood and tissue, and examples thereof may include lung cancer, gastric cancer, breast cancer, colon cancer, liver cancer, uterine cancer, esophageal cancer, skin cancer, and the like. In the treatment of cancer, surgery or radiation therapy and chemotherapy using chemotherapeutic agents that inhibit cell proliferation are main methods. Among them, gastric cancer is one of the most common malignant tumors worldwide and is known as the third leading cause of death due to cancer. In addition, it has been reported that most gastric cancer patients are in an advanced stage and have a very poor prognosis. In metastatic gastric cancer, platinum-based combination chemotherapy is considered a standard therapy, but it is known that many patients are refractory to the therapies, and the response period is as short as several months even in patients who are responsive. In addition, except for trastuzumab and ramucirumab as a secondary therapy in patients with human epidermal growth factor receptor 2 (EGFR2)-positive tumors, clinical trials on new target drugs have failed to successfully treat gastric cancer. The reason for the low survival rate in gastric cancer is that gastric cancer is a heterogeneous disease with significantly different aggression and response to the therapy and the clinical result and prognosis of each patient do not always match the reported data. The symptoms of gastric cancer show a variety of aspects from no symptoms at all to severe pain. In addition, the symptoms of gastric cancer do not have any specific characteristics, but represent general digestive symptoms. Generally, in the early stages of gastric cancer, there are almost no symptoms, and if any, the symptoms are mild enough to feel slight indigestion or upper abdominal discomfort, and thus, most people easily ignore the symptoms to cause the increased mortality of gastric cancer.

Until now, most screening methods of gastric cancer have been physical. The first method is gastrointestinal X-ray imaging, which includes double contrast, compression imaging, and mucosal imaging, and the second method is gastroscopy which may directly view the inside of the stomach by the eye not only to detect the smallest lesions that are not shown in X-ray inspection, but also to perform a direct biopsy in a place where gastric cancer is suspected, thereby increasing the diagnostic rate. However, this method has disadvantages in that the expertise of a gastroscopy operator is required, there are hygiene problems, and the patient has to endure pain while the examination is performed. Therefore, recently, studies have been conducted to diagnose gastric cancer by measuring the expression level of a gene marker specifically expressed in gastric cancer, and research on genetic markers for predicting the prognosis of gastric cancer patients is relatively less conducted.

In the related art, an anatomical observation method (the invasion degree of cancer cells and the number of metastasized lymph nodes) was used to predict the prognosis of gastric cancer patients, but the subjective judgment of doctors may be intervened, and there was a limit to accurately predicting the prognosis. In addition, in order to improve the recovery rate after gastric cancer surgery, there have been attempts to improve the survival rate of gastric cancer patients with adjuvant chemotherapy using platinum (Paoletti X. et al., JAMA 303(17): 1729~1737; Lim L. et al., J. Clin. Oncol. 23(25):6220~6232), but it has been shown that 30% to 50% of patients experience tumor recurrence after curative resection, and an effect of chemotherapy differs in terms of tumor biology (Sasako M. et al., J. Clin. Oncol. 29(33):4387~4393). Therefore, there is a demand for the development of clinical or biological predictors for applying chemotherapy to gastric cancer patients who have undergone resection.

Meanwhile, an antibody is an immune protein that binds to a specific antigen. In most mammals, including humans and mice, the antibody is formed by pairing heavy and light chain polypeptides. Each chain consists of two regions called a variable region (Fv) and a constant region (Fc). The light chain and heavy chain variable regions include antigen binding determinants of the molecule and are involved in binding to a target antigen. The constant region defines a group (or isotype) of antibodies (e.g., IgG), and is involved in binding to a plurality of Fc receptors and Fc ligands that impart a series of important functional properties called effector actions. For example, the antibody has been used as a strong therapeutic agent due to some important antibody properties, such as specificity for targets, ability to mediate immune effector mechanisms, and long serum half-lives.

DISCLOSURE

Technical Problem

An object of the present invention is to provide a novel antibody to GKN1, and to a use of the antibody for screening and diagnosis of gastric cancer.

Technical Solution

In order to achieve the object, the present invention provides an isolated antibody specifically binding to GKN1 protein or an immunologically active fragment thereof.

Further, the present invention provides an isolated nucleic acid molecule encoding the isolated antibody of the present invention or the immunologically active fragment thereof, a vector including the same, and a host cell transformed with the vector.

In addition, the present invention provides a method for preparing an antibody specific to GKN1 or an immunologically active fragment thereof.

In addition, the present invention provides a composition for screening and diagnosing gastric cancer including an isolated antibody of the present invention or an immunologically active fragment thereof.

In addition, the present invention provides a kit for screening and diagnosing gastric cancer including the composition of the present invention.

In addition, the present invention provides a method for providing information required for the diagnosis of gastric cancer.

In addition, the present invention provides a use for screening and diagnosing gastric cancer of an isolated antibody specifically binding to a single epitope located in a BRICHOS domain of GKN1 protein or an immunologically active fragment thereof.

Advantageous Effects

According to the present invention, the developed antibody specific to GKN1 specifically binds to a new epitope, and can be used to confirm the level of GKN1 protein in serum, thereby detecting (diagnosing) gastric cancer with 100% sensitivity and specificity. Thus, the antibody can be usefully used for screening and diagnosing gastric cancer.

DESCRIPTION OF DRAWINGS

FIG. 1A: Construction process of anti-GKN1 antibody;

FIG. 1B: Amino acid sequence (SEQ ID NO: 18) and nucleic acid sequence (SEQ ID NO: 35) of an anti-GKN1 antibody (scFv);

FIG. 1C: Fluorescence intensity for an epitope-like spot pattern formed by adjacent peptides around a consensus motif KGPGGPPPK (amino acids 7-15 of SEQ ID NO: 1) to which a GKN1 antibody binds; and FIG. 1D: Schematic diagram of the epitope (EKKLQGKGPGGPPPKGLMYSVNPNKV, SEQ ID NO: 1) recognized by an anti-GKN1 antibody.

FIG. 2A: ELISA standard curve of recombinant GKN1 protein as capture of anti-GKN1 monoclonal antibody;

FIG. 2B: Estimated calibration curve of assay;

FIG. 2C: GKN1 protein concentration in serum according to serum dilution; and FIG. 2D: Linear regression of GKN1 protein concentration in serum according to serum dilution.

FIG. 3A: Comparison of GKN1 protein concentration in serum between gastric cancer patient and healthy subject;

FIG. 3B: ROC curve obtained with antigen GKN1 test; and

FIG. 3C: Optimal cut-off value of GKN1 protein in serum for diagnosing gastric cancer (GC) derived by ROC curve analysis.

FIG. 4A: Comparison of GKN1 protein concentration in serum in healthy subject, patient with early gastric cancer (EGC) and patient with advanced gastric cancer (AGC);

FIG. 4B and FIG. 4C: ROC curves obtained by GKN1 protein concentrations using serum samples of EGC FIG. 4B and AGC FIG. 4C; and FIG. 4D and FIG. 4E: GKN1 protein concentrations (cut-off values) in serum for diagnosis of EGC FIG. 4D and AGC FIG. 4E derived through ROC curve analysis.

BEST MODE OF THE INVENTION

Figure 1A:
FIGS. 1A-1D are diagrams illustrating a producing process of an anti-GKN1 antibody and an epitope mapping result thereof.
Figure 1A:

Hereinafter, an embodiment of the present invention will be described in detail with reference to the accompanying drawings. However, the following embodiments are presented as examples for the present invention, and when it is determined that a detailed description of well-known technologies or configurations known to those skilled in the art may unnecessarily obscure the gist of the present invention, the detailed description thereof may be omitted, and the present invention is not limited thereto. Various modifications and applications of the present invention are possible within the description of claims to be described below and the equivalent scope interpreted therefrom.

Terminologies used herein are terminologies used to properly express embodiments of the present invention, which may vary according to a user, an operator's intention, or customs in the art to which the present invention pertains. Therefore, these terminologies used herein will be defined based on the contents throughout the specification. Throughout the specification, unless explicitly described to the contrary, when a certain part "comprises" a certain component, it will be understood to imply the inclusion of stated elements but not the exclusion of any other elements.

Throughout the present specification, general one-letter and three-letter codes for naturally existing amino acids are used, and generally allowed three-letter codes for other amino acids, such as α-aminoisobutyric acid (Aib) and N-methylglycine (Sar) are also used. The amino acids mentioned herein as abbreviations are also described as follows according to the IUPAC-IUB nomenclature.

Alanine: A, Arginine: R, Asparagine: N, Aspartic acid: D, Cysteine: C, Glutamic acid: E, Glutamine: Q, Glycine: G, Histidine: H, Isoleucine: I, Leucine: L, Lysine: K, Methionine: M, Phenylalanine: F, Proline: P, Serine: S, Threonine: T, Tryptophan: W, Tyrosine: Y, and Valine: V.

In one aspect, the present invention relates to an isolated antibody specifically binding to a single epitope located in a BRICHOS domain of gastrokine 1 (GKN1) protein or an immunologically active fragment thereof.

In an embodiment, the epitope may include an amino acid sequence represented by SEQ ID NO: 1.

In an embodiment, the isolated antibody or the immunologically active fragment thereof may include a VL domain including a complementarity determining regions light chain (CDRL)1 including an amino acid sequence represented by SEQ ID NO: 2, a CDRL2 including an amino acid sequence represented by SEQ ID NO: 3, or a CDRL3 including an amino acid sequence represented by SEQ ID NO: 4.

In an embodiment, the isolated antibody or the immunologically active fragment thereof may include a VL domain including FR1 including an amino acid sequence represented by SEQ ID NO: 8, FR2 including an amino acid sequence represented by SEQ ID NO: 9, FR3 including an amino acid sequence represented by SEQ ID NO: 10, or FR4 including an amino acid sequence represented by SEQ ID NO: 11.

In an embodiment, the isolated antibody or the immunologically active fragment thereof may include a VH domain including a complementarity determining regions heavy chain (CDRH)1 including an amino acid sequence represented by SEQ ID NO: 5, a CDRH2 including an amino acid sequence represented by SEQ ID NO: 6, or a CDRH3 including an amino acid sequence represented by SEQ ID NO: 7.

In an embodiment, the isolated antibody or the immunologically active fragment thereof may include a VH domain including FR1 including an amino acid sequence represented by SEQ ID NO: 12, FR2 including an amino acid sequence represented by SEQ ID NO: 13, FR3 including an amino acid sequence represented by SEQ ID NO: 14, or FR4 including an amino acid sequence represented by SEQ ID NO: 15.

In an embodiment, the isolated antibody or the immunologically active fragment thereof may include a VL domain including an amino acid sequence represented by SEQ ID NO: 16.

In an embodiment, the isolated antibody or the immunologically active fragment thereof may include a VH domain including an amino acid sequence represented by SEQ ID NO: 17.

In an embodiment, the isolated antibody or the immunologically active fragment thereof may include an amino acid sequence represented by SEQ ID NO: 18.

In an embodiment, the isolated antibody may be any one selected from the group consisting of a chimeric antibody, a humanized antibody, a bivalent, a bispecific molecule, a minibody, a domain antibody, a bispecific antibody, an antibody mimetic, a diabody, a triabody, or a tetrabody. The immunologically active fragment thereof may be any one selected from the group consisting of Fab, Fd, Fd', Fab', dAb, F(ab'), $F(ab')_2$, scFv (single chain fragment variable), Fv, a single chain antibody, an Fv dimer (dsFv), or a complementarity determining region (CDR) fragment, and more preferably scFv.

The antibody includes functional fragments of an antibody molecule as well as a whole antibody form. The whole antibody has a structure having two full-length light chains and two full-length heavy chains, and each light chain is linked to the heavy chain by disulfide bonds. The functional fragment of the antibody molecule refers to a fragment having an antigen-binding function. Examples of the antibody fragment include (i) an Fab fragment consisting of a light chain variable region (VL), a heavy chain variable region (VH), a light chain constant region (CL), and a first heavy chain constant region (CH1); (ii) an Fd fragment consisting of the VH and CH1 domains; (iii) an Fv fragment consisting of VL and VH domains of a single antibody; (iv) a dAb fragment consisting of a VH domain (Ward E S et al., Nature 341:544-546 (1989)); (v) an isolated CDR region; (vi) an F(ab')2 fragment, which is a bivalent fragment including two linked Fab fragments; (vii) a single-chain Fv molecule (scFv) in which the VH domain and the VL domain are linked to each other by a peptide linker to form an antigen-binding domain; (viii) a bispecific single-chain Fv dimer (PCT/US92/09965); (ix) a diabody (WO94/13804), which is a multivalent or multispecific fragment produced by gene fusion, and the like.

The antibody or the immunologically active fragment thereof of the present invention may be selected from the group consisting of animal-derived antibodies, chimeric antibodies, humanized antibodies, human antibodies, and immunologically active fragments thereof. The antibody may be produced recombinantly or synthetically.

Animal-derived antibodies produced by immunizing an animal to be immunized with a desired antigen may generally cause immune rejection when administered to humans for therapeutic purposes, and chimeric antibodies have been developed to suppress such immune rejection. The chimeric antibody is obtained by substituting a constant region of an animal-derived antibody, which causes an anti-isotype response, with a constant region of a human antibody using a genetic engineering method. Compared to animal-derived antibodies, the chimeric antibody is improved significantly in anti-isotype response, but includes the side effects on potential anti-idiotypic responses because animal-derived amino acids are still present in a variable region. The humanized antibody is developed to improve these side effects. The humanized antibody is produced by grafting complementarity determining regions (CDRs), which play an important role in antigen binding in the variable region of the chimeric antibody, to a human antibody framework.

In the CDR grafting technology for producing the humanized antibody, it is most important to select an optimized human antibody that can best accept the CDR region of the animal-derived antibody, and to this end, applications of an antibody database, analysis of a crystal structure, molecular modeling technology, etc. are used. However, even if the CDR region of an animal-derived antibody is grafted into an optimized human antibody framework, in some cases, there are amino acids that affect antigen binding while being located in the framework of the animal-derived antibody. As a result, since there are many cases in which antigen-binding ability is not preserved, it is required to apply additional antibody engineering techniques to restore the antigen-binding ability.

The antibody or the immunologically active fragment thereof may be isolated from a living body (not present in a living body) or may non-naturally occur, for example, may be synthetically or recombinantly produced.

In the present invention, the "antibody" refers to a substance produced by stimulation of an antigen in the immune system, and the type thereof is not particularly limited, and may be obtained naturally or non-naturally (e.g., synthetically or recombinantly). Antibodies are advantageous for mass expression and production because of being very stable in vivo as well as in vitro and having a long half-life. In addition, since the antibody essentially has a dimer structure, avidity is very high. An intact antibody has a structure having two full-length light chains and two full-length heavy chains, and each light chain is linked to the heavy chain by disulfide bonds. The constant region of the antibody is divided into a heavy chain constant region and a light chain constant region, and the heavy chain constant region has gamma (γ), mu (μ), alpha (α), delta (δ), and epsilon (ε) types, and subclasses include gamma 1 (γ1), gamma 2 (γ2), gamma 3 (γ3), gamma 4 (γ4), alpha 1 (α1) and alpha 2 (α2). The light chain constant region has kappa (κ) and lambda (λ) types.

As used herein, the term "heavy chain" is interpreted as meaning including a full-length heavy chain including a variable region domain VH including an amino acid sequence having a sufficient variable region sequence to impart specificity to an antigen, three constant region domains $C_{H1}$, $C_{H2}$ and $C_{H3}$ and a hinge, and fragments thereof. In addition, the term "light chain" is interpreted as meaning including a full-length light chain including a variable region domain $V_L$ including an amino acid sequence having a sufficient variable region sequence to impart specificity to an antigen and a constant region domain $C_L$, and fragments thereof.

In the present invention, the term "variable region or variable domain" refers to a part of an antibody molecule that exhibits many variations in sequence while performing a function that specifically binds to an antigen, and in the variable region, there are the complementarity determining regions CDR1, CDR2 and CDR3. A framework region (FR) portion exists between the CDRs to support a CDR ring. The "complementarity determining region" is a ring-shaped region involved in antigen recognition, and the specificity of the antibody for the antigen is determined as the sequence of this region changes.

The term "single chain fragment variable (scFv)" used herein refers to a single-chain antibody formed by expressing only a variable region of the antibody through genetic recombination, and is an antibody in a single-chain form in which the VH and VL regions of the antibody are linked to each other by a short peptide chain. The term "scFv" is intended to include an scFv fragment including an antigen-binding fragment, unless otherwise specified or otherwise understood from the context. This is obvious to those skilled in the art.

In the present invention, the term "complementarity determining region (CDR)" refers to an amino acid sequence of a hypervariable region of the heavy and light chains of immunoglobulin. The heavy and light chains may include three CDRs (CDRH1, CDRH2, CDRH3 and CDRL1, CDRL2, CDRL3), respectively. The CDRs may provide key contact residues for the antibody binding to an antigen or epitope.

In the present invention, the term "specifically binding" or "specifically recognizing" has the same meaning as commonly known to those skilled in the art, and means that an antigen and an antibody specifically interact with each other to cause an immunological response.

As used herein, the term "antigen-binding fragment" refers to a fragment of the entire structure of immunoglobulin, and refers to a portion of a polypeptide including a portion capable of binding with the antigen. For example, the antigen-binding fragment may be scFv, (scFv)2, scFv-Fc, Fab, Fab' or F(ab')2, but is not limited thereto. The Fab of the antigen-binding fragment has a structure having variable regions of the light and heavy chains, a constant region of the light chain, and a first constant region ($C_{H1}$) of the heavy chain, and has one antigen-binding domain. The Fab' is different from Fab in that the Fab' has a hinge region including one or more cysteine residues at a C-terminal of the heavy chain $C_{H1}$ domain. The F(ab')2 antibody is produced when the cysteine residues in the hinge region of Fab' form a disulfide bond. Fv is a minimal antibody fragment having only a heavy chain variable region and a light chain variable region, and a recombination technique for generating the Fv fragment is widely known in the art. The two-chain Fv has a heavy chain variable region and a light chain variable region linked by a non-covalent bond, and the single-chain Fv may generally form a dimer-like structure such as the two-chain Fv because the variable region of the heavy chain and the variable region of the single chain are covalently linked by a peptide linker or directly linked at a C-terminal. The linker may be a peptide linker consisting of 1 to 100 or 2 to 50 random amino acids, and appropriate sequences are known in the art. The antigen-binding fragment may be obtained using protease (for example, the entire antibody is restriction-cleaved with papain to obtain Fab, and cleaved with pepsin to obtain an F(ab')2 fragment), and may be produced through genetic recombination technology.

In the present invention, the term "hinge region" refers to a region included in the heavy chain of the antibody, and means a region which is present between the $C_{H1}$ and $C_{H2}$ regions and functions to provide flexibility of the antigen-binding domain in the antibody. For example, the hinge may be derived from a human antibody, specifically, derived from IgA, IgE, or IgG, such as IgG1, IgG2, IgG3, or IgG4.

In one aspect, the present invention relates to an isolated nucleic acid molecule encoding an antibody of the present invention or an immunologically active fragment thereof, a vector including the same, and a host cell transformed therewith.

In an embodiment, the isolated nucleic acid molecule may include any one selected from the group consisting of nucleotide sequences represented by SEQ ID NOs: 19 to 35.

The nucleic acid molecule of the present invention may be isolated or recombinant, and include not only DNA and RNA in single-stranded and double-stranded form, but also corresponding complementary sequences. The isolated nucleic acid is a nucleic acid that has been isolated from surrounding genetic sequences present in the genome of a subject from which the nucleic acid was isolated, in the case of a nucleic acid isolated from a naturally occurring source. In the case of a nucleic acid synthesized enzymatically or chemically from a template, such as a PCR product, a cDNA molecule, or an oligonucleotide, the nucleic acid produced from such a procedure may be understood as an isolated nucleic acid molecule. The isolated nucleic acid molecule refers to a nucleic acid molecule in the form of a separate fragment or as a component of a larger nucleic acid construct. The nucleic acid is operably linked when placed into a functional relationship with another nucleic acid sequence. For example, DNA of a pre-sequence or secretory leader is expressed as a preprotein in the form before the polypeptide is secreted, to be operably linked to DNA of the polypeptide, and a promoter or enhancer is operably linked to a coding sequence when affecting the transcription of the polypeptide sequence, or a ribosome binding domain is operably linked to a coding sequence when disposed to promote the translation. In general, it means that operably linked DNA sequences are located contiguously, and that the secretory leader exists contiguously in the same reading frame. However, the enhancer needs not to be contiguously located. The linkage is achieved by ligation at a convenient restriction enzyme site. When there is no such a site, synthetic oligonucleotide adapters or linkers are used according to conventional methods.

In the isolated nucleic acid molecule encoding the antibody of the present invention or the immunologically active fragment thereof, due to the degeneracy of codons or in consideration of codons preferred in an organism in which the antibody is to be expressed, it will be well understood by those skilled in the art that various modifications may be made to a coding region within a range without changing the amino acid sequence of the antibody to be expressed from the coding region, various modifications or changes may be made within a range without affecting the expression of the gene even in parts other than the coding region, and such modified genes are also included within the scope of the present invention. That is, as long as the nucleic acid molecule of the present invention encodes a protein having equivalent activity thereto, one or more nucleic acid bases may be mutated by substitution, deletion, insertion, or a combination thereof, which are also included in the scope of the present invention. The sequence of such a nucleic acid molecule may be single- or double-stranded, and may be a DNA molecule or an RNA (mRNA) molecule.

The isolated nucleic acid molecule encoding the antibody of the present invention or the immunologically active fragment thereof according to the present invention may be inserted into an expression vector for protein expression. The expression vector usually contains a protein operably linked, i.e., functionally related with control or a regulatory sequence, a selectable marker, an optional fusion partner, and/or an additional element. In appropriate conditions, the antibody of the present invention or the immunologically active fragment thereof may be produced by a method for inducing the protein expression by culturing a host cell transformed with a nucleic acid, preferably an expression vector containing an isolated nucleic acid molecule encoding the antibody of the present invention or the immunologically active fragment thereof. A variety of suitable host cells may be used including mammalian cells, bacteria, insect cells, and yeast, but not limited thereto. Methods for introducing exogenous nucleic acids into host cells are known in the art and will vary depending on a host cell to be used. Preferably, it is possible to produce *E. coli*, which has high industrial value due to low production cost, as a host cell.

The vector of the present invention may include a plasmid vector, a cosmid vector, a bacteriophage vector, a viral vector, etc., but is not limited thereto. The suitable vector includes a signal sequence or a leader sequence for membrane targeting or secretion in addition to expression regulatory elements such as a promoter, an operator, an initiation codon, a termination codon, a polyadenylation signal, and an enhancer and may be variously produced according to a purpose. The promoter of the vector may be constitutive or inductive. The signal sequence may use a PhoA signal sequence, an OmpA signal sequence, etc. in the case of *Escherichia* sp. bacteria as a host, an α-amylase signal sequence, a subtilisin signal sequence, etc. in the case of *Bacillus* sp. bacteria as a host, an MFα signal sequence, a SUC2 signal sequence, etc. in the case of yeast as a host, and an insulin signal sequence, an α-interferon signal sequence, an antibody molecule signal sequence, etc. in the case of an animal cell as a host, but is not limited thereto. Further, the vector may include a selective marker for selecting a host cell including a vector and a replicable expression vector includes a replication origin.

As used herein, the term "vector" refers to a vehicle into which a nucleic acid sequence may be inserted for introduction into a cell capable of replicating the nucleic acid sequence. The nucleic acid sequence may be exogenous or heterologous. The vector may include plasmids, cosmids, and viruses (e.g., bacteriophage), but is not limited thereto. Those skilled in the art may construct vectors by standard recombinant techniques (Maniatis, et al., Molecular Cloning, A Laboratory Manual, Cold Spring Harbor Press, Cold Spring Harbor, N.Y., 1988; and Ausubel et al., In: Current Protocols in Molecular Biology, John, Wiley & Sons, Inc, NY, 1994 etc.).

In an embodiment, when constructing the vector, expression regulatory sequences such as a promoter, a terminator, and an enhancer, sequences for membrane targeting or secretion, etc. are appropriately selected according to a type of host cell and may be variously combined depending on a purpose.

In the present invention, the term "expression vector" refers to a vector including a nucleic acid sequence encoding at least a portion of a gene product to be transcribed. In some cases, the RNA molecule is then translated into a protein, a polypeptide, or a peptide. The expression vector may include various regulatory sequences. In addition to regulatory sequences that regulate transcription and translation, vectors and expression vectors may also include nucleic acid sequences that serve other functions.

In the present invention, the term "host cell" includes a eukaryote and a prokaryote, and refers to any transformable organism capable of replicating the vector or expressing a gene encoded by the vector. The host cell may be transfected or transformed by the vector, which means a process in which an exogenous nucleic acid molecule is delivered or introduced into the host cell.

In an embodiment, the host cell may be a bacterial or animal cell, the animal cell line may be a CHO cell, an HEK cell or an NSO cell, and the bacteria may be *Escherichia coli*.

In one aspect, the present invention relates to a method for producing an antibody specific to GKN1 or an immunologically active fragment thereof including culturing a host cell transformed with a vector including an isolated nucleic acid molecule encoding an isolated antibody of the present invention or an immunologically active fragment thereof; and recovering the antibody or the immunologically active fragment thereof from the host cell culture.

In one aspect, the present invention relates to a composition for screening and diagnosing gastric cancer including an isolated antibody of the present invention or an immunologically active fragment thereof.

In an embodiment, the composition may be a composition for measuring the level of GKN1 protein in blood, plasma or serum, most preferably for measuring the level of GKN1 protein in serum.

In an embodiment, the measurement may be performed by a method selected from the group consisting of Western blot, enzyme linked immunosorbent assay (ELISA), radioimmunoassay (RIA), radioimmunodiffusion, immunoelectrophoresis, tissue immunostaining, immunoprecipitation assay, complement fixation assay, FACS, mass spectrometry or protein microarray, and most preferably ELISA.

In an embodiment, the composition may be used for ELISA analysis.

In an embodiment, the gastric cancer may be early gastric cancer or advanced gastric cancer.

In one aspect, the present invention relates to a kit for screening and diagnosing gastric cancer including the composition.

In an embodiment, the kit may further include not only tools and/or reagents for collecting a biological sample from a subject or patient, but also tools and/or reagents for preparing genomic DNA, cDNA, RNA or protein from the sample. For example, the kit may include a PCR primer for amplifying a relevant region of genomic DNA. The kit may include a probe of a genetic factor useful for pharmacogenomic profiling. In addition, in the use of such a kit, labeled oligonucleotides may be used for easy identification during analysis.

In an embodiment, the kit may further contain DNA polymerase and dNTP (dGTP, dCTP, dATP and dTTP), a labeling substance such as a fluorescent substance.

In one aspect, the present invention relates to a method for providing information required for diagnosing gastric cancer, including measuring the level of GKN1 protein in a biological sample isolated from a test subject.

In an embodiment, the method may further include determining that a test subject has gastric cancer when the level of GKN1 protein is 6.608 ng/ml or less.

In an embodiment, the biological sample may be blood, plasma or serum, more preferably serum.

In an embodiment, the gastric cancer may be early gastric cancer or advanced gastric cancer.

In an embodiment, the level of GKN1 protein may be measured by an ELISA assay, and the optimal concentration of the anti-GKN1 antibody of the present invention for measuring the level of GKN1 protein in serum by the ELISA assay may be 0.5 μg/ml, and an optimal dilution of the serum may be 100-fold.

In an aspect, the present invention provides a use for screening and diagnosing gastric cancer of an isolated antibody that specifically binds to a single epitope located in a BRICHOS domain of GKN1 protein or an immunologically active fragment thereof.

MODES OF THE INVENTION

Hereinafter, the present invention will be described in more detail with reference to the following Examples. However, the following Examples are only intended to embody the contents of the present invention, and the present invention is not limited thereto.

Example 1. Construction of Anti-GKN1 Monoclonal Antibodies

To develop anti-GKN1 monoclonal antibodies, a phage display test method with selectivity and specificity for a specific antigen was used. Specifically, human recombinant GKN1 protein was immobilized on a solid phase, and then cultured on the surface of M13 bacteriophage with an scFv phage library expressing heavy and light chain variable domains of various antibodies. Unbound phages were washed, and high-affinity phages were eluted from the immobilized antigen. The eluted phages were incubated with *E. coli* host cells and infected into the cells and a subpopulation of phages expressing an antibody with affinity for GKN1 was amplified. The panning process was repeated three times. Colonies of infected bacteria were incubated on a plate, a monoclonal scFv (single-chain variable fragment) was produced from each colony, and then monoclonal scFvs specifically binding to recombinant GKN1 protein were selected as independent clone units (95 in total) using ELISA. Among them, 5 antibodies without Fc and BSA background were obtained, and among them, a monoclonal conjugate with the lowest BSA background was amplified by PCR and inserted into a mini-body (scFv-Fc) expression vector. Thereafter, the recombinant plasmid was transfected into 293F cells and the monoclonal mini-body was purified using affinity chromatography (FIG. 1A).

Figure 1B:

Example 2. Analysis of Anti-GKN1 Monoclonal Antibodies 2-1. Identification of Sequences of Heavy and Light Chain Variable Regions The amino acid sequences of heavy and light chain variable domains (regions) of the anti-GKN1 antibody prepared in Example 1 were determined. Specifically, phagemid DNA of the anti-GKN1 antibody was extracted and DNA sequences of the heavy and light chain variable domains of the anti-GKN1 antibody were determined using PCR-sequencing (ABI3730XL, Sanger-method sequencing, Phred Score>20) (primer sequence: forward: 5'-AAGACAGCTATCGCGATTGCAG-3' and reverse: 5'-GCCCCCTTATTAGCGTTTGCCATC-3'), and then the sequences of VL, linker, VH, and complementarity determining regions (CDRs) of the antibody were indicated (FIG. 1B).

2-2. Epitope Mapping

In order to examine the potential and antigen specificity of the anti-GKN1 antibody prepared in Example 1, linear epitopes of the antibody were mapped using PEPperMAP® technology (PEPperPRINT GmbH, Heidelberg, Germany), a microarray technology including 199 peptides. Specifically, to avoid truncated peptides, the C-terminal and N-terminal of the sequence of GKN1 (UniProtKB Q9NS71) were extended with a neutral GSGSGSG linker. The extended antigen sequence was translated into a linear 15-amino acid peptide with a 14 amino acid peptide-peptide overlap. After peptide synthesis, all peptides were cyclized through a thioether linkage between cysteine of the C-terminal and an appropriately modified N-terminal. A conformational GKN1 peptide microarray was constructed so as to include 199 different peptides (398 peptide spots) printed in duplicate and further include human influenza hemagglutinin (HA, YPYDVPDYA, 76 spots) control peptide. A hybridoma supernatant containing the anti-GKN1 antibody was diluted with an incubation PBS buffer (pH 7.4, with 0.005% Tween 20) and a 10% MB-070 blocking buffer (Rockland Immunochemicals, Limerick, Pennsylvania, USA), and incubated with the peptide microarray at 4° C. at 140 rpm for 16 hours. The array was washed with a washing buffer (PBS, pH 7.4, with 0.005% Tween 20) to remove unbound antibodies. Thereafter, the peptide array was stained with goat anti-human IgG (H+L) conjugated with 0.2 μg/mL of DyLight680 (Thermo Fisher Scientific). HA control peptides framing the peptide array were stained with 0.5 μg/mL of monoclonal anti-HA (12CA5)-DyLight800 (Thermo Fisher Scientific) for 45 minutes at room temperature. Spot intensities and peptide annotations were quantified using the LI-COR Odyssey Imaging System (scanning offset 0.65 mm, resolution 21 μm, and scanning intensities of 7/7 (red=700 nm/green=800 nm)) and PepSlide Analyzer.

Figure 1C:
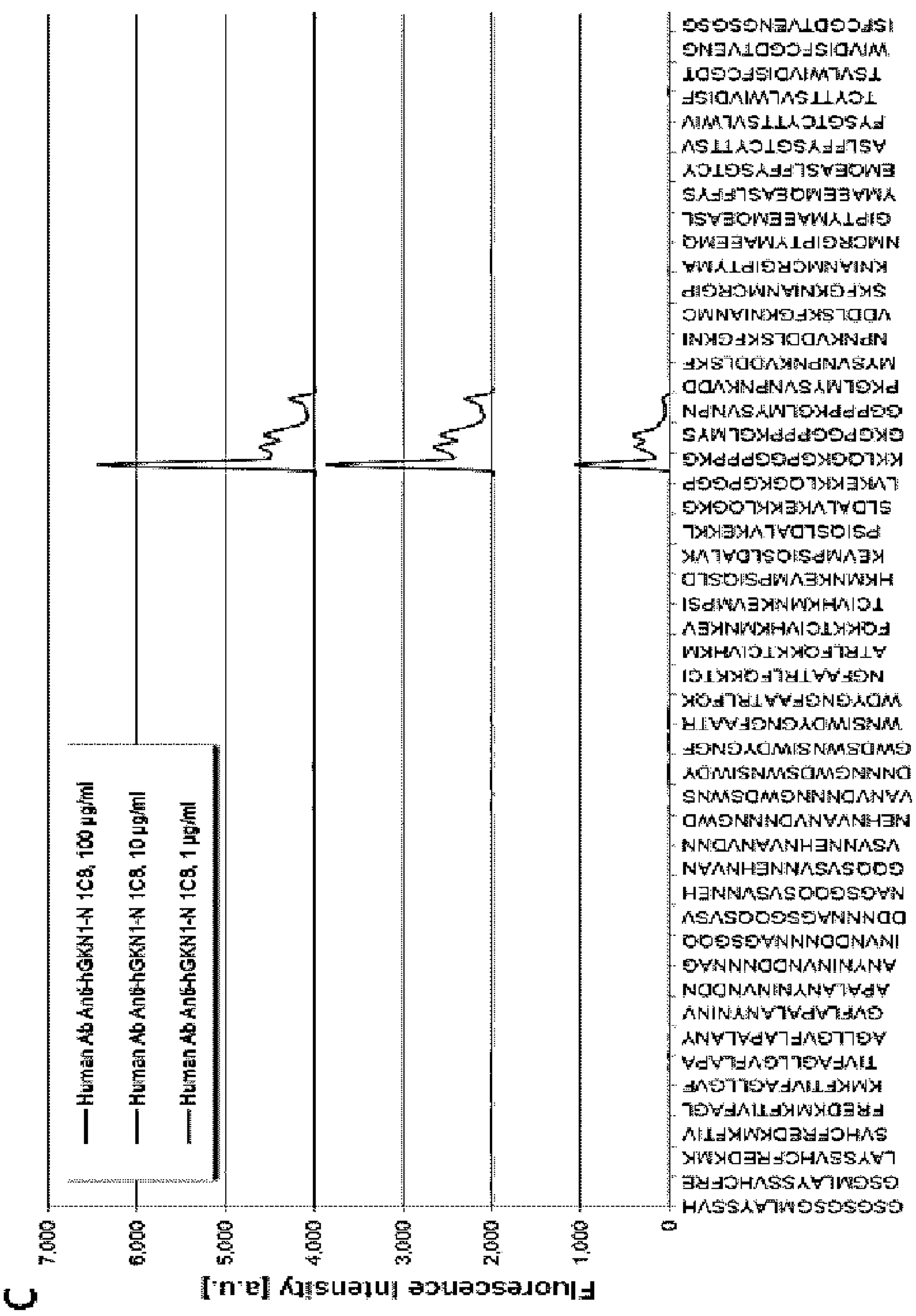
Figure 1D:
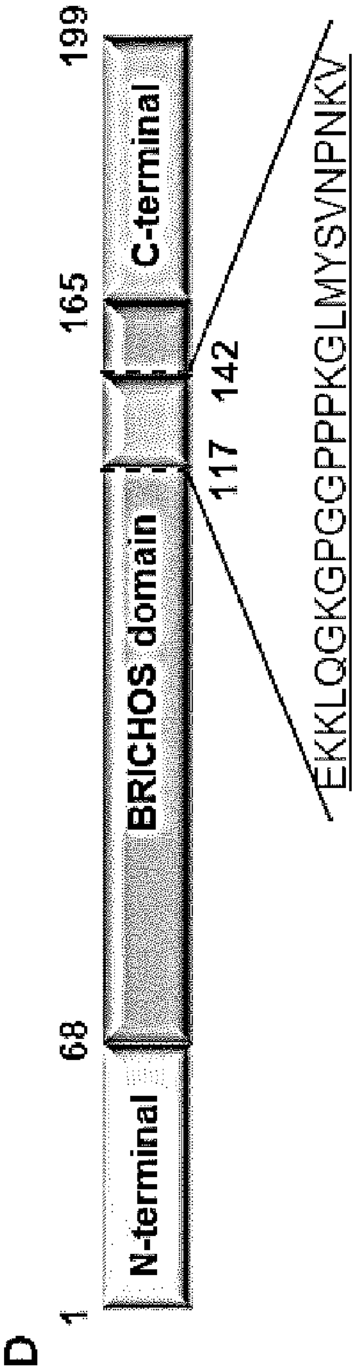

In addition, as a result of incubating another human GKN1 peptide microarray copy with the human anti-GKN1 antibody, spot patterns were shown in contiguous peptides around a consensus motif KGPGGPPPK (amino acids 7-15 of SEQ ID NO: 1) in a signal-to-noise ratio (FIG. 1C). As a result of mapping epitopes based on these signal patterns, the antibody produced in the present invention showed a clear monoclonal antibody response recognizing a single epitope (EKKLQGKGPGGPPPKGLMYSVNPNKV, SEQ ID NO: 1) located in a BRICHOS domain of the GKN1 protein (FIG. 1D).

Example 3. Optimization of Serum GKN1 ELISA Assay 3-1. Construction of Anti-GKN1-FITC Conjugate The anti-GKN1 monoclonal antibody of the present invention was labeled using a FluoReporter FITC Protein Labeling Kit (Molecular Probes). The (component A) amount of a FITC-labeled dye was variously configured (1, 3 and 10 μL of reaction volumes), and based on A280 and A494 absorbance reading values, a fluorescence:antibody (F:A) ratio was calculated according to the instructions of the kit, including a recommended correction factor for the absorbance of the dye at 280 nm.

3-2. Optimization of Concentration of Anti-GKN1 Antibody

The applicability of a GKN1 sandwich ELISA assay method for measuring the concentration of GKN1 in serum was confirmed using recombinant GKN1 protein, and sera derived from healthy subjects and gastric cancer patients. Specifically, serum samples were collected from 500 gastric cancer patients, including 350 advanced gastric cancer (AGC) patients and 150 early gastric cancer (EGC) patients classified according to the depth of invasion, and control healthy volunteers (n=200), and no evidence of familial cancer was found in any of the patients. To normalize the total protein amount in the serum samples, the total protein concentration in serum was adjusted to 15 μg/ml using PBS. Thereafter, since the GKN1 protein existed as an exosomal protein in human serum, the serum samples were incubated at 70° C. for 10 minutes. In addition, in order to optimize the antibody concentration of the present invention, the anti-GKN1 monoclonal antibody was serially diluted to 0.25, 0.5, 1 and 2 μg/ml, and a coefficient of variation (CV) was estimated in a logistic regression model using softMaxPro. For optimization of ELISA conditions, assay parameters were evaluated, such as conditions for achieving a large positive antecedent association ($R^2$>0.8), and limit of detection (LOD), lower limit of quantification (LOQ) and dilution linearity of recombinant GKN1 protein, human serum and anti-GKN1 antibody. In addition, a microtiter plate was coated with another anti-GKN1 monoclonal antibody (H7) prepared in Example 1 and sealed with an adhesive sealing film for a microplate (ImmunoChemistry Technologies, Minn., USA). The wells were blocked with 300 μl/well of a blocking solution, and then the plate was incubated in the dark for 1 hour at room temperature. Thereafter, the plate was washed twice with a PBST buffer. Thereafter, the serum samples prepared above and the recombinant GKN1 protein were put into each well and incubated at 37° C. for 1 hour. Thereafter, the wells were washed with PBS three times, added with an anti-GKN1 monoclonal antibody conjugated with FITC, and then incubated at room temperature for 2 hours. The level of GKN1 in serum was determined using a Synergy H1 plate reader ELISA reader (Bio-Tek) at an excitation wavelength of 485 nm and an emission wavelength of 528 nm.

Figure 2A:
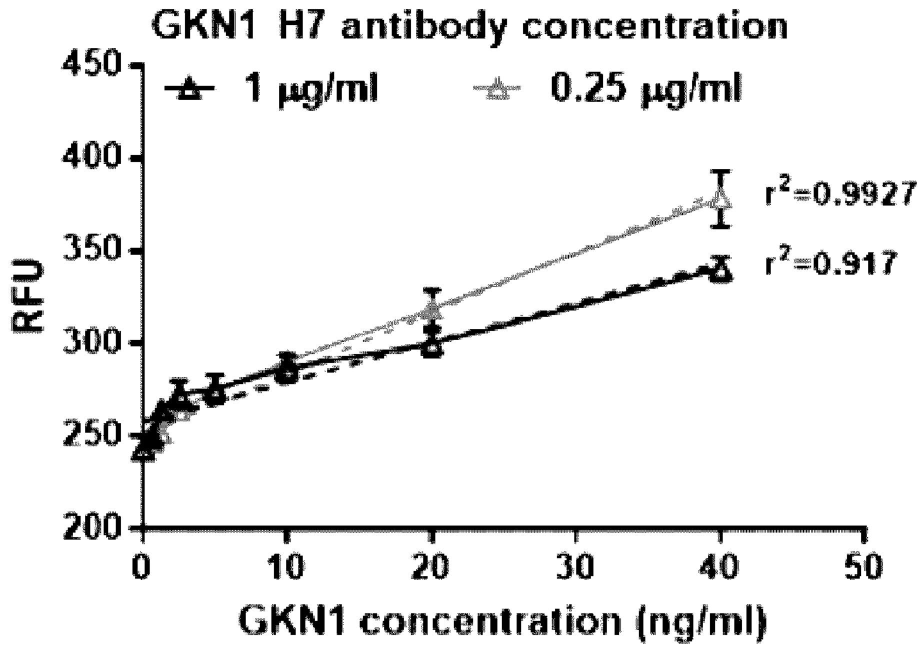
FIGS. 2A-2D are diagrams illustrating the determination of an anti-GKN1 antibody and a serum dilution factor for measuring a GKN1 concentration in serum using a sandwich ELISA assay.
Figure 2B:
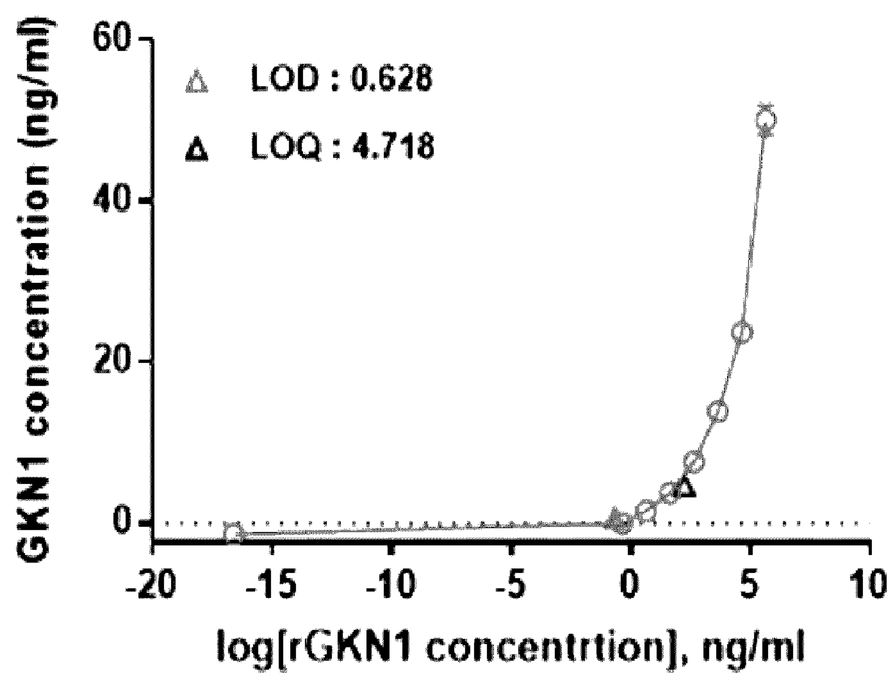

For Sandwich ELISA analysis, another anti-GKN1 antibody (H7) selected in Example 1 was diluted 6,800-fold (0.25 μg/ml), coated on a microplate, and then the ELISA values obtained with the anti-GKN1 antibody of the present invention conjugated to FITC using the recombinant GKN1 protein were highly consistent with the values of the anti-GKN1 antibody (H7) diluted 1:1,700 times (1 μg/ml) (FIG. 2A). In addition, in a serial dilution calculation curve of the recombinant GKN1 protein, linear regression analysis of the result versus predicted recombinant GKN1 concentration derived a correlation coefficient of 0.993 (FIG. 2A). The H7 anti-GKN1 antibody was diluted 6,800-fold (0.25 μg/ml) and coated on a microplate, and in sandwich ELISA analysis using recombinant GKN1 protein as a calibrator and the anti-GKN1 antibody of the present invention conjugated to FITC, variation coefficients (CV) were 0.39 to 1.69 for the recombinant GKN1 protein and 0.98 for the PBS sample. In addition, the LOD was 0.628 ng/ml and the LOQ was 4.718 ng/ml (FIG. 2B). In addition, it was confirmed that to measure the level of GKN1 in serum, the optimal concentration of the anti-GKN1 antibody of the present invention was 0.5 μg/ml.

3-3. Optimization of Serum Dilution

Figure 2C:
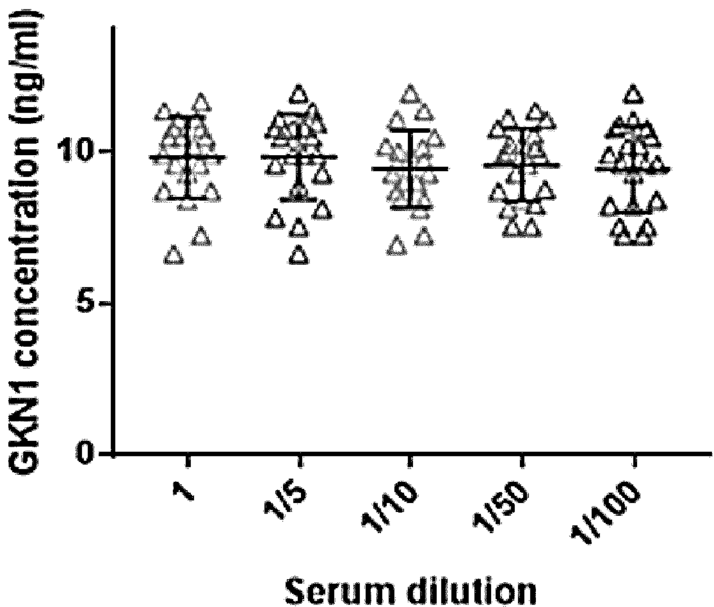
Figure 2D:
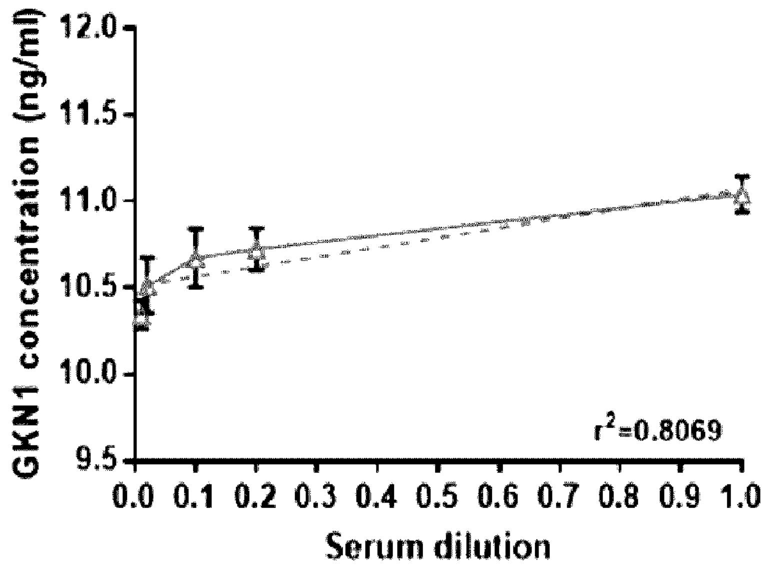

Serum dilution concentrations of 1:5, 1:10, 1:50 and 1:100 of 20 different healthy sera were evaluated to determine the optimal dilution of the sera. As a result, the mean±SD of serum GKN1 concentrations in serum diluted at 1:1 and 1:100 was 9.799±1.33 ng/ml and 9.42±1.41 ng/ml, respectively, and serum dilution analysis results also showed similar values, with CVs of 13.52 to 14.96, $r^2$=0.8069, and s/n ratios=7.3 to 6.7 (FIGS. 2C and 2D). Through this, it was confirmed that the optimal dilution of serum for minimizing non-specific responses due to IgG in serum in ELISA analysis was 100-fold dilution.

Example 4. Diagnosis of Gastric Cancer Using GKN1 ELISA Analysis Values in Serum 4-1. Confirmation of Diagnosis of Gastric Cancer Through ELISA Analysis of GKN1 in Serum As in Example 3, the levels of GKN1 in serum samples from healthy subjects and gastric cancer patients were confirmed by ELISA analysis. To optimize the diagnostic usefulness of the anti-GKN1 sandwich ELISA kit, receiver-operator characteristic (ROC) curve analysis was performed, and an optimal cutoff level of serum GKN1 concentration for detecting gastric cancer was determined using the analysis. Based on the cut-off value of the GKN1 protein level in the serum, sensitivity (true positive fraction; TPF), specificity (true negative fraction; TPF), FNF (false negative fraction), FPF (false positive fraction), PPV (positive predictive value), NPV (negative predictive value), accuracy, LR+ (positive likelihood ratio), LR− (negative likelihood ratio) and DOR (diagnostic odds ratio) were determined.

TABLE 1

| | Normal | GC |
|---|---|---|
| Total number of values | 200 | 500 |
| Number of excluded values | 0 | 0 |
| Number of binned values | 200 | 500 |
| Minimum | 6.647119 | 0.196452 |
| 25% Percentile | 8.16617825 | 1.369301 |
| Median | 9.1132825 | 2.068348 |
| 75% Percentile | 10.16566 | 3.175605 |
| Maximum | 14.85706 | 6.569125 |
| Mean | 9.257044175 | 2.336775896 |
| Std. Deviation | 1.38913902409222 | 1.53617993839418 |
| Std. Error of Mean | 0.0982269623946472 | 0.0687000553584164 |
| Lower 95% CI of mean | 9.06334487368692 | 2.20179887807635 |
| Upper 95% CI of mean | 9.45074347631308 | 2.47175291392365 |

TABLE 2

| | Fromula | Calculation | Estimate |
|---|---|---|---|
| Sensitivity | TP/(TP + FN) | 500/500 | 1 |
| Specificity | TN/(TN + FP) | 200/200 | 1 |
| PPV | TP/(TP + FP) | 500/500 | 1 |
| NPV | TN/(TN + FN) | 200/200 | 1 |
| LR+ | Sensitivity/(1 − Specificity) | 1/(1 − 1) | 0 |
| LR− | (1 − Sensitivity)/Specificity | (1 − 1)/1 | 0 |
| Accuracy | (TP + TN)/(TP + FP + TN + FN) | 700/700 | 1 |
| DOR | LR+/LR− | 0/0 | 0 |

Figure 3A:
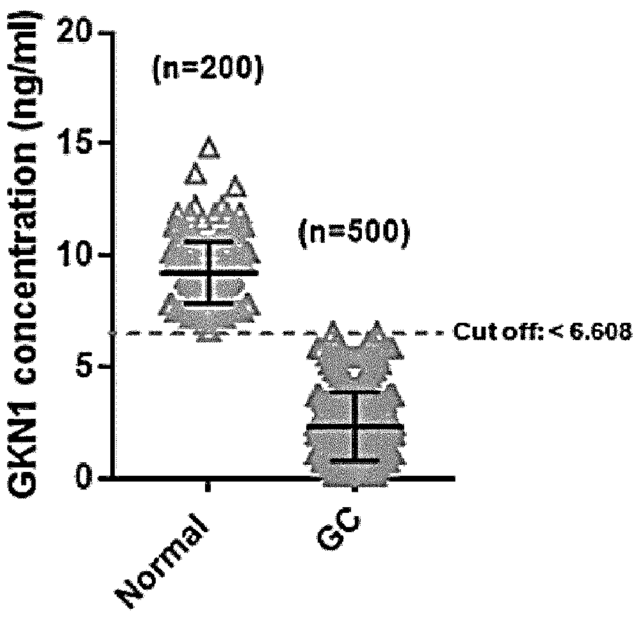
FIGS. 3A-3C are diagrams of confirming the diagnostic performance of GKN1 protein in serum in ELISA analysis.
Figure 3B:
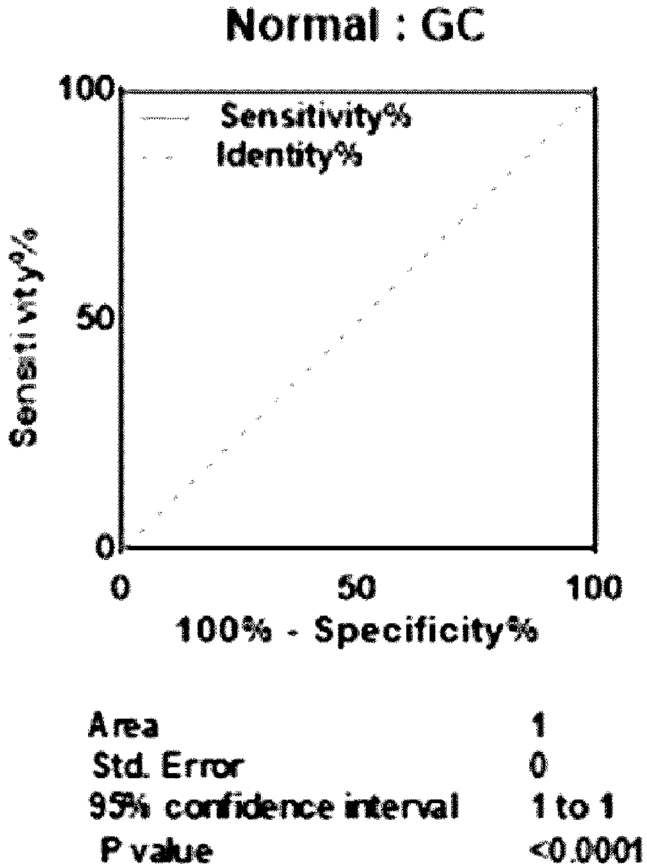
Figure 3C:
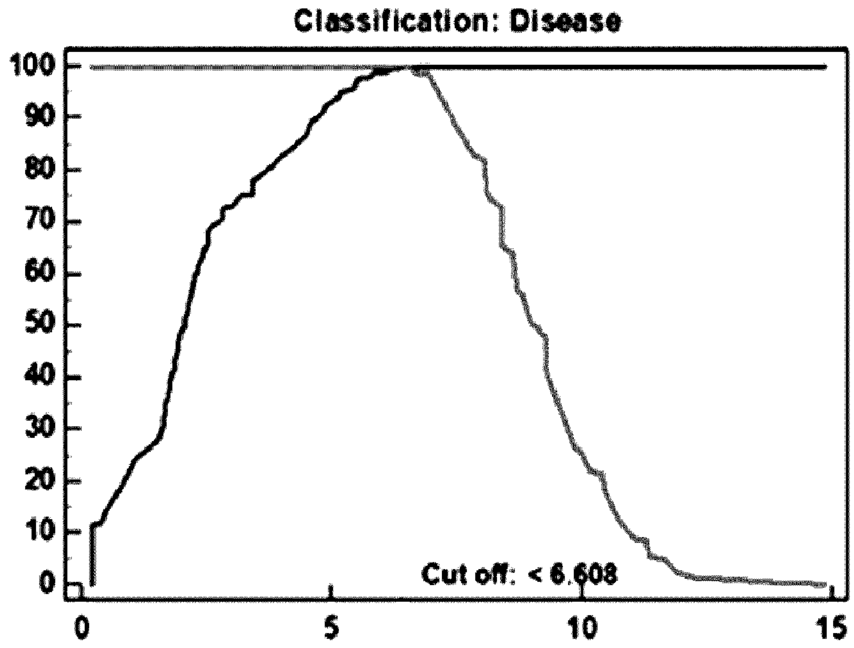

As a result of confirming the level of GKN1 in serum by ELISA analysis using the anti-GKN1 antibody of the present invention, it was found that the levels of GKN1 in serum were significantly lower in gastric cancer patients (2.33±1.53 ng/ml) than in healthy subjects (9.25±1.38 ng/ml) (FIG. 3A and Table 1). In addition, in order to confirm whether the GKN1 protein in serum may be applied as a marker for screening and early diagnosis of gastric cancer, ROC curve analysis was performed. As a result, it was confirmed that the level of GKN1 protein in serum was shown to completely distinguish between healthy individuals and gastric cancer patients with an AUC value of 1.0000 (FIG. 3B), and the GKN1 level in serum of 6.608 ng/ml was identified as an optimal cut-off value for diagnosis of gastric cancer (FIG. 3A). The serum GKN1 protein levels in all 200 controls exceeded the cut-off value, whereas the serum GKN1 protein levels in 500 gastric cancer patients were below the cut-off value (FIG. 3A and Table 1). At this cut-off value, the sensitivity and specificity for gastric cancer diagnosis were 100% and 100%, respectively (FIG. 3B and Table 2), and PPV and NPV were also 100% and 100%, respectively (Table 2). In addition, the diagnostic accuracy and DOR at the GKN1 cut-off value in serum were 1 and 0, respectively (Table 2). Accordingly, it can be seen that ELISA analysis of the GKN1 protein in serum using the anti-GKN1 antibody of the present invention can be used as a screening or diagnosis tool for gastric cancer with very high sensitivity and specificity.

Figure 4A:
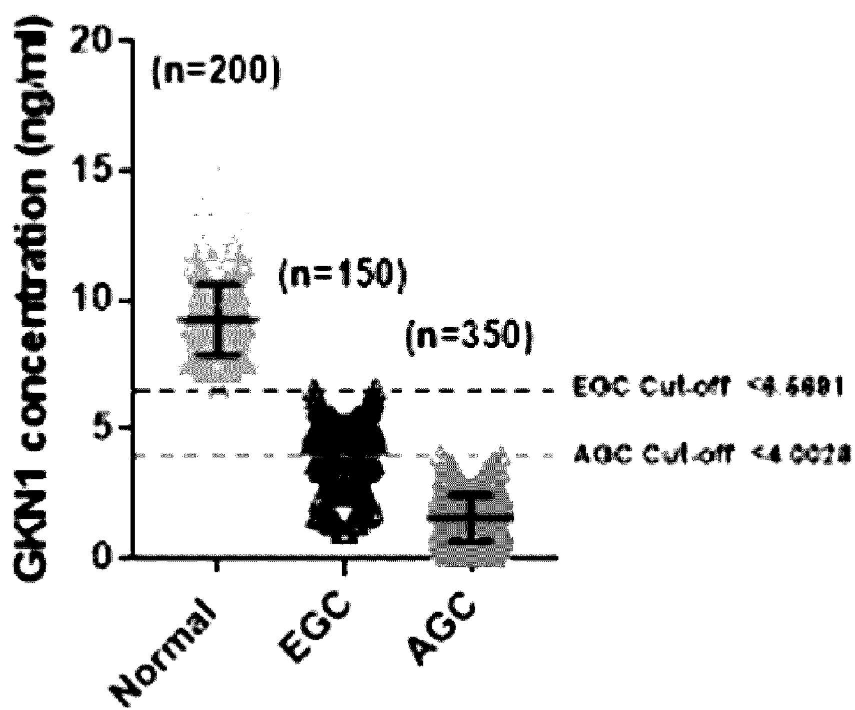
FIGS. 4A-4E are diagrams of confirming the diagnostic performance of GKN1 protein in serum in patients with early gastric cancer and advanced gastric cancer.
Figure 4B:
Figure 4B:
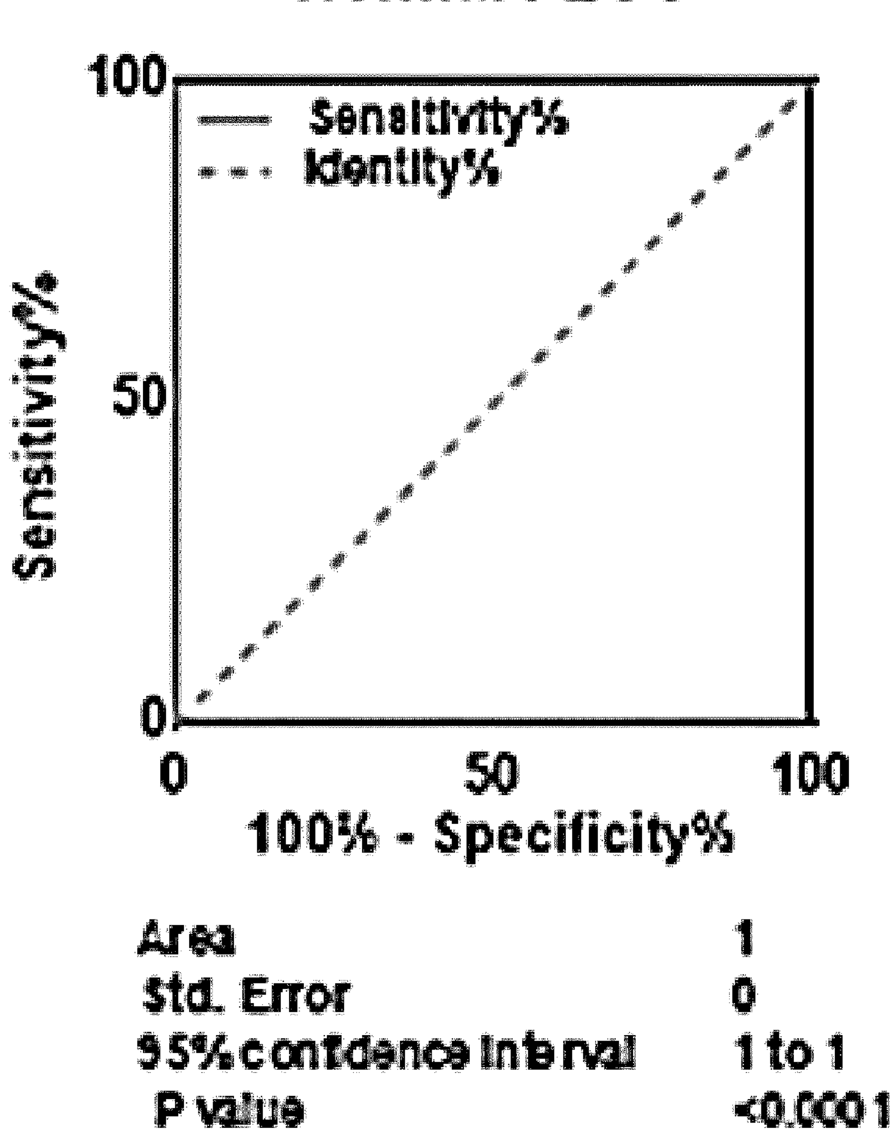
Figure 4C:
Figure 4C:
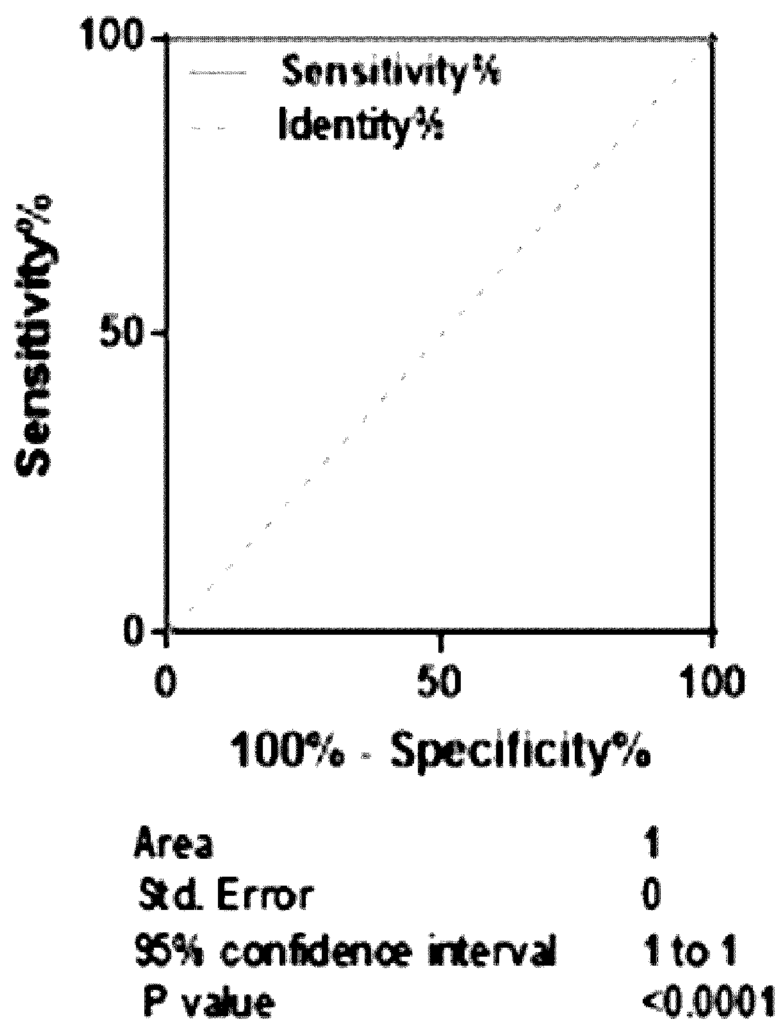
Figure 4D:
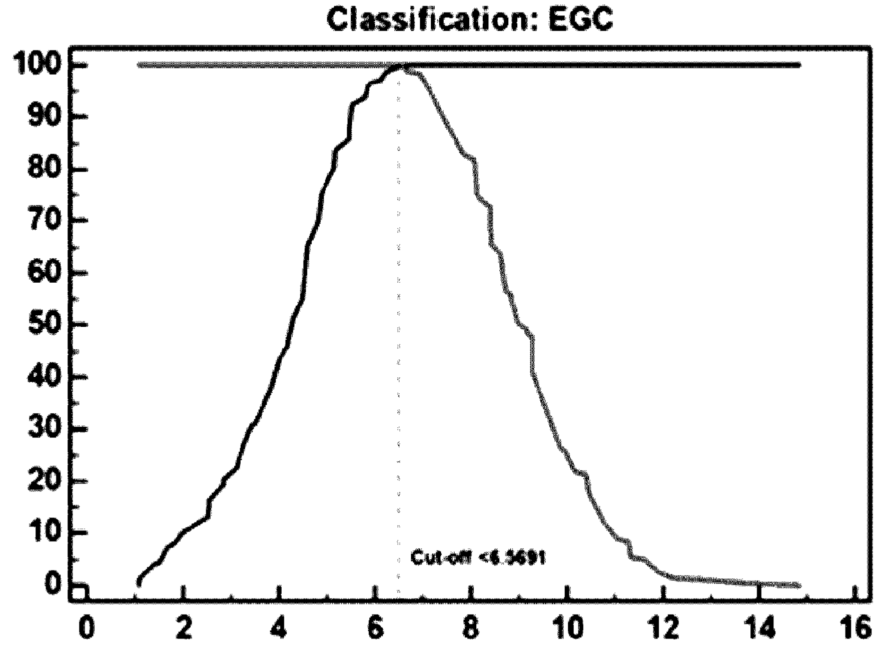
Figure 4E:
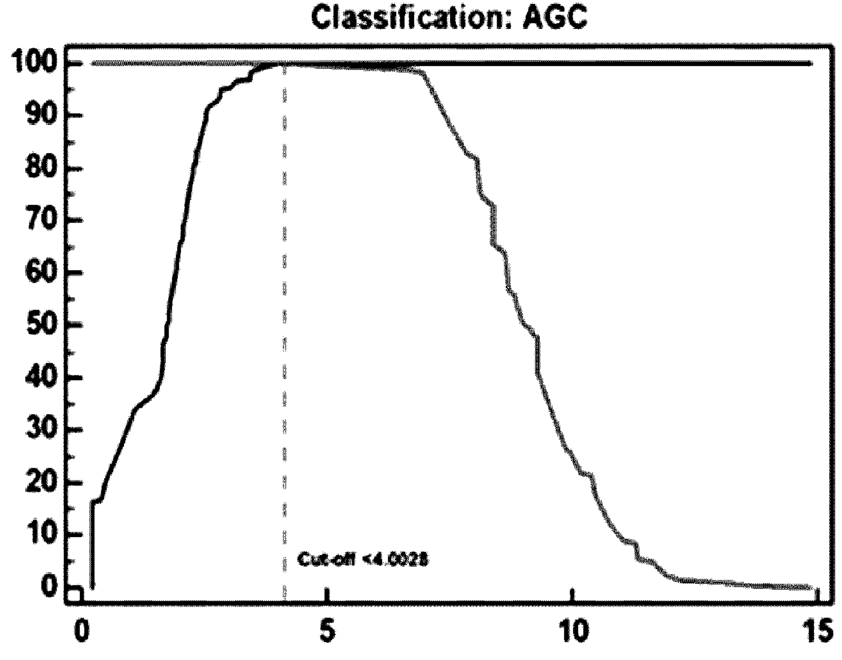

4-2. Identification of Discrimination Between Advanced Gastric Cancer and Early Gastric Cancer As a result of confirming whether the ELISA analysis of the GKN1 protein in serum using the anti-GKN1 antibody of the present invention may also distinguish the progression degree of gastric cancer, it was shown that the levels of GKN1 protein in serum were 4.085±1.27 ng/ml for EGC and 1.587±0.895 ng/ml for AGC, which were significantly lower than those of healthy subjects, and particularly, the level of GKN1 protein in serum in an AGC patient group was lower than that in an EGC patient group (FIG. 4A and Table 3). In addition, ROC curve analysis showed that the level of GKN1 in serum clearly distinguished both EGC and AGC from healthy subjects, and AUC values were 1.00 (AUC 95% CI=0.990 to 1.000) and 1.00 (AUC 95% CI=0.993 to 1.000), respectively (FIGS. 4B and 4C). In addition, as a result of ROC analysis, the optimal diagnostic cut-off values of GKN1 level in serum for diagnosing EGC and AGC from healthy subjects were 6.5691 ng/ml (sensitivity 99% and specificity 100%) and 4.0028 ng/ml (sensitivity 99% and specificity 100%), respectively (FIGS. 4A and 4B, Table 4). However, when the cut-off value of the GKN1 protein in serum for the two gastric cancers was selected as 6.608 ng/ml, both the sensitivity and specificity for EGC were 100%, and both the sensitivity and specificity for AGC were 100% (FIGS. 4A and 4B, Table 5). In addition, the diagnostic accuracy of the GKN1 cut-off value in serum was 1 for both EGC and AGC (Table 5).

TABLE 3

| | Normal | EGC | AGC |
|---|---|---|---|
| Total number of values | 200 | 150 | 350 |
| Number of excluded values | 0 | 0 | 0 |
| Number of binned values | 200 | 150 | 350 |
| Minimum | 6.647119 | 1.076089 | 0.196452 |
| 25% Percentile | 8.16617825 | 3.36024075 | 0.782876 |
| Median | 9.1132825 | 4.301422 | 1.731154 |
| 75% Percentile | 10.16566 | 4.952382 | 2.203225 |
| Maximum | 14.85706 | 6.569125 | 4.00821 |
| Mean | 9.257044175 | 4.08559606 | 1.58728154 |
| Std. Deviation | 1.38913902409222 | 1.27583486064583 | 0.895169618343944 |
| Std. Error of Mean | 0.09822696239464 | 0.10417148015457 | 0.047848828784174 |
| Lower 95% CI of mean | 9.06334487368692 | 3.87975184247403 | 1.4931732024938 |
| Upper 95% CI of mean | 9.45074347631308 | 4.29144027752597 | 1.6813898775062 |

TABLE 4

| | | Normal vs EGC (cut-off value = 6.5691 ng/ml) | | Normal vs AGC (cut-off value = 4.0028 ng/ml) | |
|---|---|---|---|---|---|
| Measure | Formula | Calculation | Estimate | Calculation | Estimate |
| Sensitivity | TP/(TP + FN) | 148/150 | 0.99 | 348/350 | 0.94 |
| Specificity | TN/(TN + FP) | 200/200 | 1 | 200/200 | 1 |
| PPV | TP/(TP + FP) | 148/148 | 1 | 348/348 | 1 |
| NPV | TN/(TN + FN) | 200/202 | 0.99 | 200/202 | 0.99 |
| LR+ | Sensitivity/(1 − specificity) | 0.99/(1 − 1) | 0 | 0.994/(1 − 1) | 0 |
| LR− | (1 − sensitivity)/specificity | (1 − 0.99)/1 | 0.01 | (1 − 0.994)/1 | 0.006 |
| Accuracy | (TP + TN)(TP + FP + TN + FN) | 348/350 | 0.99 | 548/550 | 0.996 |
| DOR | LR+/LR− | 0/0.01 | 0 | 0/0.006 | 0 |

TABLE 5

| Measure | Formula | Normal vs EGC (cut-off value = 6.608 ng/ml) | | Normal vs AGC (cut-off value = 6.608 ng/ml) | |
|---|---|---|---|---|---|
| | | Calculation | Estimate | Calculation | Estimate |
| Sensitivity | TP/(TP + FN) | 150/150 | 1 | 350/350 | 1 |
| Specificity | TN/(TN + FP) | 200/200 | 1 | 200/200 | 1 |
| PPV | TP/(TP + FP) | 150/150 | 1 | 350/350 | 1 |
| NPV | TN/(TN + FN) | 200/200 | 1 | 200/200 | 1 |
| LR+ | Sensitivity/(1 − specificity) | 1/(1 − 1) | 0 | 1/(1 − 1) | 0 |
| LR− | (1 − sensitivity)/specificity | (1 − 1)/1 | 0 | (1 − 1)/1 | 0 |
| Accuracy | (TP + TN)/(TP + FP + TN + FN) | 350/350 | 1 | 550/550 | 1 |
| DOR | LR+/LR− | 0/0 | 0 | 0/0 | 0 |

The invention claimed is:

1. An isolated antibody specifically binding to a single epitope located in a BRICHOS domain of gastrokine 1 (GKN1) protein or an immunologically active fragment thereof, comprising:

a light chain variable domain (VL) including a complementarity determining region light chain (CDRL) 1 including the amino acid sequence represented by SEQ ID NO: 2, a CDRL2 including the amino acid sequence represented by SEQ ID NO: 3, and a CDRL3 including the amino acid sequence represented by SEQ ID NO: 4; and a heavy chain variable domain (VH) including a complementarity determining region heavy chain (CDRH) 1 including the amino acid sequence represented by SEQ ID NO: 5, a CDRH2 including the amino acid sequence represented by SEQ ID NO: 6, and a CDRH3 including the amino acid sequence represented by SEQ ID NO: 7.

2. The isolated antibody or the immunologically active fragment thereof of claim 1, wherein the epitope includes an amino acid sequence represented by SEQ ID NO: 1.

3. The isolated antibody or the immunologically active fragment thereof of claim 1, comprising: a VL domain including framework region (FR) 1 including the amino acid sequence represented by SEQ ID NO: 8, FR2 including the amino acid sequence represented by SEQ ID NO: 9, FR3 including the amino acid sequence represented by SEQ ID NO: 10, and FR4 including the amino acid sequence represented by SEQ ID NO: 11.

4. The isolated antibody or the immunologically active fragment thereof of claim 1, comprising: a VH domain including framework region (FR) 1 including the amino acid sequence represented by SEQ ID NO: 12, FR2 including the amino acid sequence represented by SEQ ID NO: 13, FR3 including the amino acid sequence represented by SEQ ID NO: 14, and FR4 including the amino acid sequence represented by SEQ ID NO: 15.

5. The isolated antibody or the immunologically active fragment thereof of claim 1, comprising a VL domain including the amino acid sequence represented by SEQ ID NO: 16.

6. The isolated antibody or the immunologically active fragment thereof of claim 1, comprising a VH domain including the amino acid sequence represented by SEQ ID NO: 17.

7. The isolated antibody or the immunologically active fragment thereof of claim 1, comprising the amino acid sequence represented by SEQ ID NO: 18.

8. A composition for screening and diagnosing gastric cancer comprising the isolated antibody or the immunologically active fragment thereof of claim 1.

9. A kit for screening and diagnosing gastric cancer comprising the composition of claim 8.

10. An isolated nucleic acid molecule encoding the isolated antibody or the immunologically active fragment thereof of claim 1.

11. The isolated nucleic acid molecule of claim 10, comprising any one selected from the group consisting of nucleotide sequences represented by SEQ ID NOs: 19 to 35.

12. A vector comprising the isolated nucleic acid molecule of claim 10.

13. A host cell transformed with the vector of claim 12.

14. A method for producing an antibody specific to GKN1 or an immunologically active fragment thereof comprising:

a) culturing a host cell transformed with a vector including an isolated nucleic acid molecule encoding the isolated antibody or the immunologically active fragment thereof of claim 1; and b) recovering the antibody or the immunologically active fragment thereof from the host cell culture.

* * * * *